Figure 1:
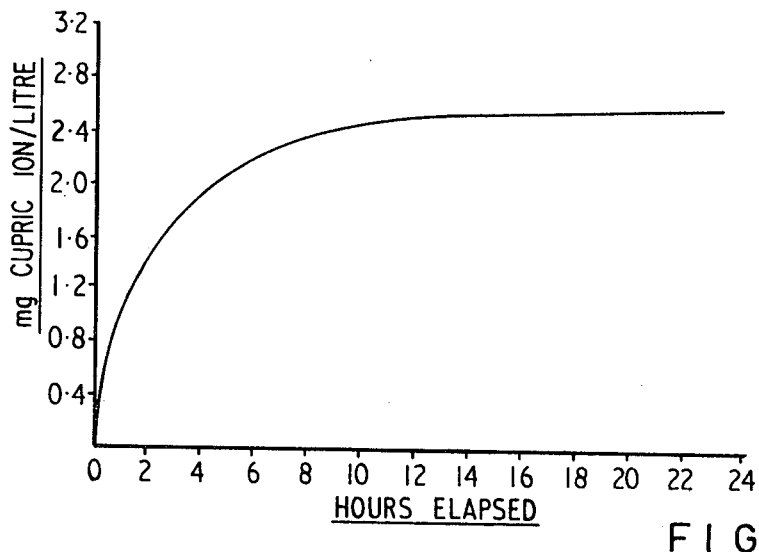

United States Patent [19]

Hughes et al.

[11] 4,447,254

[45] May 8, 1984

[54] CONTROLLED RELEASE OF TRACE ELEMENTS

[75] Inventors: Alan C. Hughes, Liverpool; Richard C. Copeman; Thomas N. R. Marples, both of Chester, all of England

[73] Assignee: McKenchnie Chemicals Limited, West Midlands, England

[21] Appl. No.: 285,699

[22] Filed: Jul. 22, 1981

[30] Foreign Application Priority Data

Jul. 24, 1980 [GB] United Kingdom ................. 8024324
Sep. 5, 1980 [GB] United Kingdom ................. 8028801
Feb. 12, 1981 [GB] United Kingdom ................. 8104390
Feb. 12, 1981 [GB] United Kingdom ................. 8104391

[51] Int. Cl.$^3$ ..................... A01N 59/20; A01N 59/00; A61K 33/34
[52] U.S. Cl. ......................................... 71/67; 424/14; 424/19; 424/22; 424/127; 424/131; 424/133; 424/134; 424/140; 424/141; 424/143; 424/144; 424/145; 424/147; 424/357; 424/150; 424/151; 426/2; 426/74; 426/648
[58] Field of Search ................. 424/14, 127, 357, 131, 424/133, 134, 140, 141, 143, 144, 145, 150, 154, 357; 426/2, 66, 74, 648, 86, 591, 477; 71/67

[56] References Cited

U.S. PATENT DOCUMENTS

| | | | |
|---|---|---|---|
| 1,649,123 | 11/1927 | Miner et al. | 426/74 |
| 1,712,404 | 5/1929 | Rupp | 426/74 |
| 2,792,345 | 5/1957 | Hulsebosch | 424/14 |
| 2,810,229 | 10/1957 | Allyn | 71/67 |
| 3,056,723 | 10/1962 | Galloway | 424/14 |
| 3,056,724 | 10/1962 | Marston | 424/22 |
| 3,130,124 | 4/1964 | Ferris et al. | 71/67 |
| 3,276,949 | 10/1966 | Robson | 424/22 |
| 3,322,633 | 5/1967 | Simoons | 424/22 |
| 4,187,803 | 2/1980 | Valenta | 424/357 |
| 4,325,975 | 4/1982 | Lindon et al. | 424/127 |

FOREIGN PATENT DOCUMENTS 1176196 1/1970 United Kingdom .

*Primary Examiner*—Sam Rosen
*Attorney, Agent, or Firm*—William A. Drucker

[57] ABSTRACT

A composition for providing a substantially controlled level of dissolved trace element in water comprises a trace element compound in a relatively insoluble form. Preferably the composition comprises a relatively insoluble trace element compound and a binder which results in the composition having a different solubility product to that of the trace element alone. The binder may be plaster of paris.

21 Claims, 6 Drawing Figures

CONTROLLED RELEASE OF TRACE ELEMENTS

This invention concerns controlled release of trace elements into water, particularly but not exclusively into animal drinking water.

Trace elements, such as copper, cobalt and selenium are a necessary part of the diet of livestock. For example, copper deficiency is recognized as a major cause of poor growth and ill health of cattle. It is believed that a fully grown cow requiers from 65 to 250 mg of copper per day to maintain a healthy level of copper.

0.08 to 0.1 mg of cobalt/1 kg of dry matter in the feed intake is required by livestock to prevent a deficiency in vitamin B12. In addition from 0.05 to 0.08 mg of selenium/1 kg of dry matter in the feed intake is required by livestock to prevent a deficiency in vitamin E.

Supplementing the diet of housed cattle is readily accomplished by including trace element compounds in their feed. However, this is difficult to achieve evenly for grazing cattle.

Parenteral administration of copper compounds has been proposed but this is time consuming and expensive, since it involves frequent handling of the animals.

Offering grazing animals copper containing minerals on a free choice basis has also been proposed but this results in a wide variation of copper intake from animal to animal. Also, a high intake of copper can be dangerous so that this uncontrolled administration of copper is also not satisfactory from the point of view of safety.

The simplest way of administering a trace element, such as copper, to animals is clearly via their water supply, since all animals must drink and for example, a fully grown cow will usually drink 30 to 40 liters of water per day. Therefore, apart from measuring out the required amount of soluble copper, e.g. in the form of copper sulphate, no further supervision is needed. However, there is the possibility that an animal may drink too much water and hence take in a dangerous amount of copper.

It has been proposed to provide metering devices connected to a water supply and which will dispense a fixed amount of soluble copper into the water fed into a drinking trough. These metering devices are expensive and also difficult to move from field to field, unless one is installed in each field thus further increasing the expense.

This invention seeks to provide a means of adding a trace element, such as copper, to a water supply in a controlled manner.

According to this invention there is provided a composition comprising a trace element compound in a relatively insoluble form, whereby the addition of the composition to water results in a substantially controlled level of dissolved trace element.

This invention also provides a method of providing a substantially controlled level of dissolved trace element in water comprising adding to the water a composition comprising a trace element in a relatively insoluble form.

Preferably such a composition comprises a relatively insoluble trace element compound mixed with a binder.

Trace elements which may be incorporated in the composition of the invention include copper, cobalt magnesium, manganese, zinc, selenium, iron, nickel, arsenic, chromium, vanadium, iodine and fluorine. Any suitable relatively insoluble compound of the above trace element may be used. For a copper based composition suitable relatively insoluble copper compounds include copper hydroxide, copper carbonate, copper oxychloride, cuprous oxide, cupric oxide, basic copper sulphate (formed by the reaction of copper sulphate with lime) and basic copper carbonate (formed by the reaction of copper sulphate with sodium carbonate). For cobalt, suitable relatively insoluble compounds include cobalt oxides, $Co_2O_3$ or $Co_3O_4$, cobalt carbonate, cobalt hydroxide, cobalt iodide, basic cobalt carbonate and basic copper sulphate. For selenium, suitable relatively insoluble compounds include selenium oxide and selenium sulphide.

Soluble trace element compounds may be used in the compositions of the invention provided that, when mixed with the binder, they result in a composition having a low controlled solubility. Examples of such soluble trace element compounds include sodium selenite and sodium selenate.

Any suitable binder or mixture of binders may be used but preferably the binder is one which when mixed with the trace element compound will provide a composition having a different solubility product to that of the trace element compound. Thus the binder and trace element can be chosen so as to provide a desired solubility product. Advantageously the binder is one which will form a settable composition which can be moulded into solids blocks or tablets.

Furthermore it is desirable that the binder be non-toxic and chemically stable with respect to time, heat and water.

For aesthetic and identification reasons, the binder is preferably white so that the natural color of the trace element compound provides the color of the composition or so that coloring of the composition is facilitated.

A preferred binder is or substantially comprises $CaSO_4.\frac{1}{2}H_2O$, such as plaster of paris.

When compositions of the invention are added to animal drinking water, contaminants, such as deposits of mud, clay, organic matter and the like, in the water can suppress the level of dissolved trace elements. It is believed that such contaminants have a matrix form which takes up certain ions. For example, copper ions are taken up by mud and the like.

Advantageously the compositions of the invention will include a compound which will prevent the trace element ions being taken up by contaminants.

The prevention of trace element ion take up by contaminants may be achieved in one of two ways. A compound may be used which blocks sites on the contaminant matrix in preferance to the trace element ions. Alternatively a compound may be used which will complex trace element ions and so keep them in solution.

The choice of blocking/complexing compound may depend on the trace element in the composition. For example, for a copper based composition, a phosphate such as sodium hexametaphosphate, is suitable. The amount of blocking/complexing compound in the compositions of the invention need only be fairly small, say 0.75 to 1.0% by weight but the amount chosen may depend on the trace element and on the amount of dissolved trace element required.

Further substances may be added to the compositions of the invention to alter the solubility and rate of dissolution of the trace element compound as desired. If it is desired to retard the dissolution rate of the trace element compound a retarder, such as a silicone or stearic acid or a salt thereof, such as magnesium or calcium stearate may be added to the composition. On the other hand, it may be desired to increase the rate of dissolution of the trace element compound, in which case accelerators such as lignosulphonate, reducing sugars, ethylene glycol or basic compounds, such as slaked lime, may be added to the composition. Examples of reducing sugars are fructose and glucose.

The compounds according to the invention may be produced in any suitable way. Mixing of the constituents of the compositions with water followed by moulding and drying has been found to be satisfactory. However, the drying temperatures must not be so high as to cause degradation. Temperatures up to 60° C., preferably from 30° to 40° C., over a period of about 14 to 16 hours are believed to be suitable.

The compositions of the invention may be produced in any suitable shape or form although it will be appreciated that surface area and texture may affect solubility rates. Conveniently the composition may be formed into blocks, slabs, tablets or granules which can be placed in a water trough, preferably in a permeable container or membrane to prevent an animal swallowing the whole block or slab or a large amount of tablets or granules. This will also reduce the amount of suspended insoluble trace element compound resulting in the water trough on disintegration of the block, slab, tablets or granules and prevent collection of the binder on the floor of the trough.

In a preferred embodiment the compositions of the invention are in the form of tablets which are sold in packets having say a one week supply. The user then empties the contents of the packet into a permeable container which he places in a water trough. At the end of the week, the container is removed from the trough, washed out and filled with another weeks supply of tablets.

When forming blocks etc. using plastic of paris as the binder it has been found advantageous to include a small amount of a substance to improve the workability of the plaster of paris. Suitable such substances are sodium citrate and sodium hexametaphosphate.

The compositions of the invention when added to water provide a substantially constant level of dissolved trace element in the water and significantly this level is different to, usually lower than the expected solubility of the trace element compound alone. For example, a composition of basic copper sulphate (hydrate) and plaster of paris will provide a level of between 2.8 to 4.2 mg cupric ion per liter of water (depending on the ratio of components), whereas basic copper sulphate alone would provide of the order of 13 to 14 mg cupric ion per liter. The mechanism by which this is achieved is probably by a lattice modification of the binder compound resulting in new trace element solubility characteristics.

Hence this invention provides a convenient and safe method of supplying animals with trace elements by controlling the amount of trace element in their water supply to a level of their necessary intake and below that which will adversely affect them, even though the total addition may contain a harmful amount of trace element.

As well as dietary requirement of certain animals trace elements such as copper can be used to kill harmful molluscs and algae. Thus, the compositions of the invention may be used to kill snails and flukeworm and so be useful in trout farming. Also, the compositions of the invention may be of benefit to oyster production or even in waterway clearance by being used to kill algae.

The trace element compound and binder should be chosen so as to provide a level of dissolved trace element which is not harmful to animals other than those to be killed. For example, a copper level of 2 ppm is effective in killing snails etc but higher levels are harmful to trout and oysters.

It will be appreciated that various factors may influence the level of dissolved trace element provided in water by the compositions of the invention, such as water hardness. The compounds present in water which cause hardness may compete with trace elements ions for the available blocking/complexing compound, if present. Also different types of animals have different trace elements requirements. Thus the amounts of the constituents of the compositions of the invention may be chosen so as to provide the required levels of dissolved trace element.

This invention will now be further described by means of the following examples:

EXAMPLE 1

A 100 g cylindrical block was prepared by mixing 25 g of "hydrate", 75 g of plaster of paris ($CaSO_4.\frac{1}{2}H_2O$) and 50 ml of water. The resultant mixture was placed in a mould and dried in an oven at 50°–60° C. for about 16 hours. ("Hydrate" is the reaction product of copper sulphate solution with a lime suspension).

In order to evaluate the properties of this block, it was placed in a tank containing one liter of water and the cupric ion content of the water measured at intervals. After 24 hours, the water was drained off and replaced by a liter of fresh water and again the cupric ion content measured at intervals. This was repeated for a third day.

Figure 2:
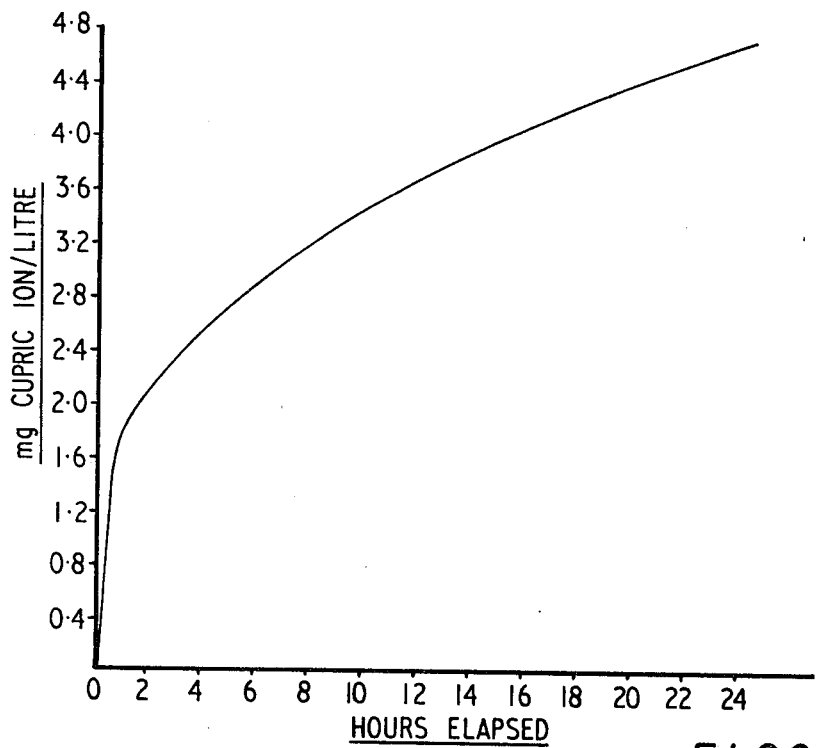
Figure 3:
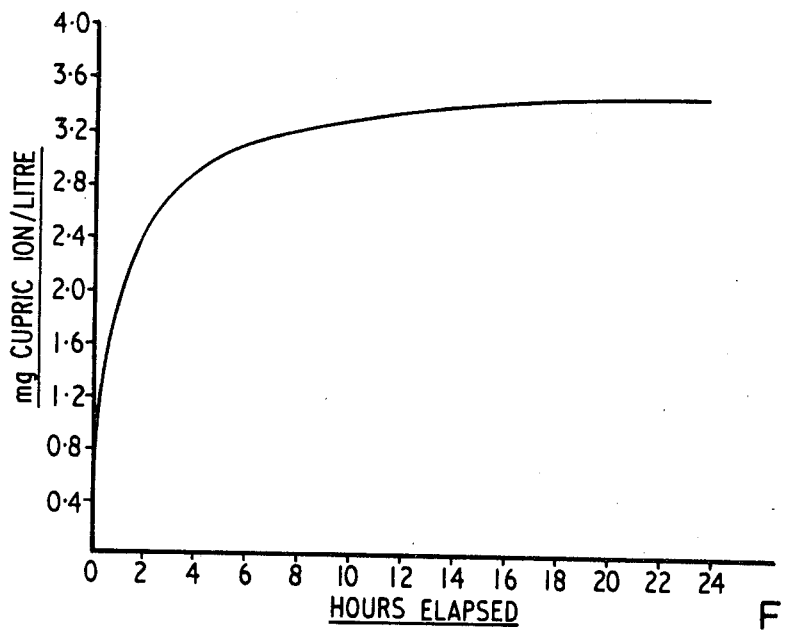

The reults are shown in the accompanying drawings in which:

FIGS. 1, 2 and 3 are plots of mg cupric ion/liter against hours elapsed for the first day, second and third days respectively.

As can be seen from the drawings, each day the cupric ion content rose rapidly over the first two to three hours but then settled at a fairly constant value for the remainder of the day. This compares favourable with the situation in a field drinking trough where water is drunk by the animals and replaced by fresh water. The highest cupric ion content reached was on day two at 4.6 mg liter. The maxima on days one and three being 2.6 and 3.7 repectively.

Under normal circumstances the solubility product of "hydrate" is about 13 to 14 mg cupric ion/liter. Therefore, it is significant that the incorporation of hydrate in a matrix substantially lowers the solubility product and maintains this at a fairly constant level.

It is believed that a copper intake of 5 mg per liter of water each day is required for say cows and it can be seen that the example block would provide a major portion of this intake and, allowing for the presence of suspended copper, the full intake requirement.

Tests have also been carried out on similar blocks to that of the above Example but with different ratios of "hydrate" to plaster of paris. These tests suggest that ratios of 25:75 hydrate to plaster of paris and less give a generally constant level of dissolved copper but that higher proportions of hydrates tend to result in some initial disintegration of the blocks.

EXAMPLE 2

Tablets (approximately 1 g each) were made from a composition of 125 g hydrate (27% Cu), 231 g plaster of paris, and 1 g sodium citrate were added to 1 liter of water and provided a level of dissolved copper of 4.8 ppm. The addition of 4 g of mud to the water reduced this level to 0.6 ppm.

1. g sodium hexametaphosphate added to this water increased the level of copper to 4.8 ppm.

(Hydrate is the reaction product of copper sulphate solution with a lime suspension).

EXAMPLE 3

Tablets (approximately 1 g each) were made from a composition of the following ingredients:

| Hydrate | 112 g |
|---|---|
| Sodium Citrate | 0.25 g |
| Sodium Hexametaphosphate | 2 g |
| Plaster of paris | 85.75 g |

These tablets provided 4 to 5 ppm of dissolved copper when added to water and were sufficient for 25 cows for 1 week.

EXAMPLE 4

Tablets (approximately 0.7 g each) were made by moulding and drying a mixture of 595.7 g plaster of paris, 1.3 g selenium sulphide, 235 mls. water and 33 m s. of a 0.5% weight aqueous solution of sodium hexametaphosphate.

Figure 4:
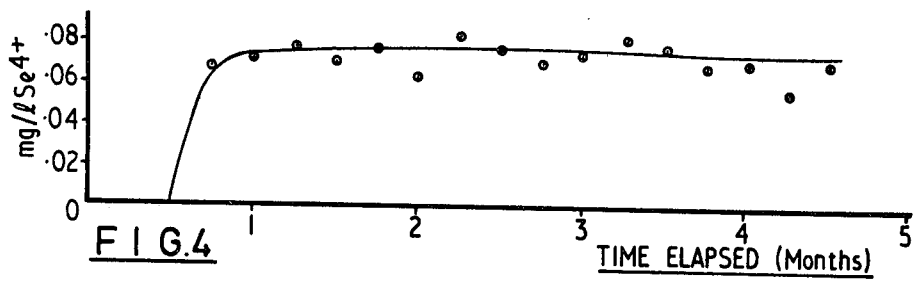

The results of field trails on such tablets are shown in FIG. 4. The tablets were placed in a permeable container in an animal drinking trough and the amount of dissolved selenium in samples of the water was measrured at intervals of about one week. As the water in the trough was being drunk by the animals it was replenished. As can be seen, the amount of dissolved selenium remained at about 0.07 mg/1. The slight variations in the amounts are probably caused by the actual time at which the results were taken, i.e. if the results were taken just after replenishment of the water, the amount of selenium would be low but if taken just prior to replenishment the amount would be high.

EXAMPLE 5

Tablets (approximately 0.7 g each) were made by moulding and drying a mixture of 596.7 g plaster of paris 1.3 g coblate carbonate, 235 mls water and 33 mls of a 0.5% by weight solution of sodium hexametaphosphate.

Figure 5:
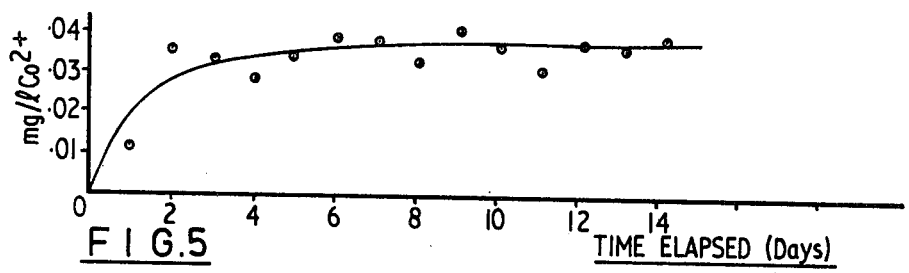

The results of field trails (as described in Example 4) on such tablets are shown in FIG. 5 except that the amout of dissolved cobalt was measured each day. As can be seen the amount of dissolved cobalt remained fairly constant at about 0.036 mg/l.

EXAMPLE 6

Tablets (approximately 0.7 g each) were made by moulding and drying a mixture of 329.1 g hydrate 27% Cu), 270.9 g plaster of paris, 365 mls. water and 33 mls. of 0.5% by weight solution of sodium hexametaphosphate.

Figure 6:
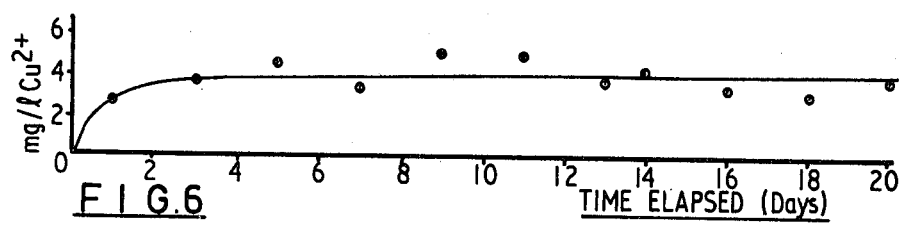

The results of field trails (as described in Example 4) on such tablets are shown in FIG. 6, except that the amount of dissolved copper was measured every two days. As can be seen the amount of dissolved copper remained fairly constant at about 4 mg/1.

We claim:

1. A method of employing in water a composition for releasing a controlled concentration of trace elements therein comprising a relatively water insoluble trace element compound and a plaster of paris binder mixed with said trace element and which mixture provides in water a composition having a different solubility product for the trace element compound.

2. A method as claimed in claim 1 wherein the trace element is selected from the group consisting of copper, cobalt, magnesium, manganese, zinc, selenium, ion, nickel, arsenic, chromium, vanadium, iodine and fluorine.

3. A method as claimed in claim 2 wherein the trace element is copper.

4. A method as claimed in claim 3 wherein the trace element compound is selected from the group consisting of copper hydroxide, copper carbonate, copper oxychloride, cuprous oxide, cupric oxide basic copper sulphate, and basic copper carbonate.

5. A method as clamed in claim 2 wherein the trace element is cobalt.

6. A method as claimed in claim 5 wherein the trace element compound is selected from the group consisting of cobalt oxide ($Co_2O_3$ or $Co_3O_4$), cobalt carbonate, cobalt hydroxide, cobalt iodide, basic cobalt carbonate and basic cobalt sulphate.

7. A method as claimed in claim 2 wherein the trace element is selenium.

8. A method as claimed in claim 7 wherein the trace element compound is selected from the group consisting of selenium oxide, selenium sulphide, sodium selenite and sodium selenate.

9. A method as claimed in claim 1 wherein the binder is one which will form a settable mouldable composition.

10. A method as claimed in claim 1 wherein the binder is non-toxic and chemically stable with respect to time, heat and water.

11. A method as claimed in claim 1 which includes a composition to prevent the trace element ions being taken up by contaminants.

12. A method as claimed in claim 11 which includes a compound which blocks sites on said contaminant matrix in preferance to trace elements ions.

13. A method as claimed in claim 11 which includes a compound which complexes the trace element ions and so keeps them in solution.

14. A method as claimed in claim 11 wherein the trace element is copper and the blocking/complexing compound is a phosphate.

15. A method as claimed in claim 14 wherein the phosphate is sodium hexametaphosphate.

16. A method as claimed in any one of claims 11 to 15 wherein the amount of blocking/complexing compound is from 0.75 to 1.0% by weight of the composition.

17. A method as claimed in claim 1 which includes a substance to retard the rate of dissolution of the trace element compound.

18. A method as claimed in claim 17 wherein said retarder is selected from the group consisting of silicones, stearic acid and salts thereof.

19. A method as claimed in claim 1 which includes a substance to accelerate the rate of dissolution of the trace element compound.

20. A method as claimed in claim 19 wherein said accelerator is selected from the group consisting of lignosulphonates, reducing sugars, ethylene glycol and basic compounds.

21. A method as claimed in claim 1 wherein the composition is in the form of tablets.

* * * * *